United States Patent
Ariely (10) Patent No.: US 11,404,166 B2
(45) Date of Patent: Aug. 2, 2022

(54) SYSTEMS AND METHODS FOR MINING OF MEDICAL DATA

(71) Applicant: Medial Research Ltd., Kfar-Malal (IL)

(72) Inventor: Ofer Ariely, Tel-Aviv (IL)

(73) Assignee: Medial Research Ltd., Kfar Malal (IL)

( * ) Notice: Subject to any disclaimer, the term of this patent is extended or adjusted under 35 U.S.C. 154(b) by 203 days.

(21) Appl. No.: 16/336,133

(22) PCT Filed: Sep. 27, 2017

(86) PCT No.: PCT/IL2017/051086
§ 371 (c)(1),
(2) Date: Mar. 25, 2019

(87) PCT Pub. No.: WO2018/060996
PCT Pub. Date: Apr. 5, 2018

(65) Prior Publication Data
US 2019/0214147 A1    Jul. 11, 2019

Related U.S. Application Data

(60) Provisional application No. 62/400,651, filed on Sep. 28, 2016.

(51) Int. Cl.
*G16H 50/30* (2018.01)
*G16H 10/40* (2018.01)
(Continued)

(52) U.S. Cl.
CPC ............ *G16H 50/30* (2018.01); *G16H 10/40* (2018.01); *G16H 50/20* (2018.01); *G16H 50/70* (2018.01);
(Continued)

(58) Field of Classification Search
USPC .......................................... 705/2–4
See application file for complete search history.

(56) References Cited

U.S. PATENT DOCUMENTS

| 8,160,901 B2 | 4/2012 | Heywood et al. |
| 2003/0018633 A1 * | 1/2003 | Horn ........................ G06F 17/18 |

(Continued)

FOREIGN PATENT DOCUMENTS

| IT | 2003-157387 | * | 1/2003 | ........... A61B 5/0452 |
| JP | 07-296089 | | 11/1995 | |

(Continued)

OTHER PUBLICATIONS

Zaninetti, Carlo, et al. "Personalized reference intervals for platelet count reduce the number of subjects with unexplained thrombocytopenia." Haematologica 100.9 (2015): e338. (Year: 2015).*

(Continued)

*Primary Examiner* — Mark Holcomb (57) ABSTRACT

There is provided a method for creating a personalized reference interval (PRI), comprising: receiving a digital profile of a patient including demographic parameters and associated values, and medical history data parameters and associated values; receiving a clinical test result including a measured value of at least one analyte; accessing a dataset storing digital profiles of other patients; identifying a subset of the dataset based a correlation according to a similarity requirement between demographic parameter(s) of the patient and of other patients, and between the medical history of the patient and the other patients; calculating a PRI for each respective analyte of the clinical test result of the patient according to an analysis of corresponding values of the analyte of the subset, wherein the PRI is dynamically calculated using the most updated version of the dataset.

18 Claims, 5 Drawing Sheets

(51) Int. Cl.
  *G16H 50/70* (2018.01)
  *G16H 50/20* (2018.01)
  *G16H 80/00* (2018.01)
  *G16H 10/60* (2018.01)
  *G16H 20/00* (2018.01)

(52) U.S. Cl.
  CPC ............. *G16H 80/00* (2018.01); *G16H 10/60* (2018.01); *G16H 20/00* (2018.01)

(56) References Cited

U.S. PATENT DOCUMENTS

| | | | |
|---|---|---|---|
| 2008/0294350 | A1 | 11/2008 | Rosano et al. |
| 2009/0062624 | A1* | 3/2009 | Neville ............... G16H 50/20 600/300 |
| 2012/0265550 | A1* | 10/2012 | Friedlander ........... G06Q 10/06 705/2 |
| 2014/0006039 | A1* | 1/2014 | Khan ................ G16H 50/30 705/2 |
| 2014/0236491 | A1* | 8/2014 | Katayev ............... G16H 50/70 702/19 |
| 2015/0254430 | A1 | 9/2015 | Oosawa et al. |

FOREIGN PATENT DOCUMENTS

| | | |
|---|---|---|
| JP | 2002-024401 | 1/2002 |
| JP | 2003-501194 | 1/2003 |
| JP | 2009-193148 | 8/2009 |
| WO | WO 2014/006862 | 1/2014 |
| WO | WO 2014/084294 | 6/2014 |
| WO | WO 2015/179861 | 11/2015 |
| WO | WO 2018/060996 | 4/2018 |

OTHER PUBLICATIONS

Supplementary European Search Report and the European Search Opinion dated May 15, 2020 From the European Patent Office Re. Application No. 17855162.8. (13 Pages).
Drukier et al. "High-Sensitivity Blood-Based Detection of Breast Cancer by Multi Photon Detection Diagnostic Proteomics", Journal of Proteome Research, XP055350821, 5(8): 1906-1915, Published on Web Jul. 14, 2006.
Edwards et al. "Laboratory Data", Clinical Pharmacy and Therapeutics, XP055691104, 5th Ed., Chap.6: 76-95, Jan. 2012.
Shah et al. "High Sensitivity Cardiac Troponin and the Under-Diagnosis of Myocardial Infarction in Women: Prospective Cohort Study", BMJ, XP055691127, 350: g7873-1-g7873-8, Published Online Jan. 21, 2015.
Communication Pursuant to Article 94(3) EPC dated Feb. 22, 2021 From the European Patent Office Re. Application No. 17855162.8. (9 Pages).
International Preliminary Report on Patentability dated Apr. 11, 2019 From the International Bureau of WIPO Re. Application No. PCT/IL2017/051086. (6 Pages).
International Search Report and the Written Opinion dated Dec. 31, 2017 From the International Searching Authority Re. Application No. PCT/IL2017/051086. (10 Pages).
Notice of Reason(s) for Rejection dated Sep. 14, 2021 From the Japan Patent Office Re. Application No. 2014-513308 and Its Translation Into English. (16 Pages).
Summons to Attend Oral Proceedings Pursuant to Rule 115(1) EPC dated Sep. 20, 2021 From the European Patent Office Re. Application No. 17855162.8. (12 Pages).
Decision to Refuse a European Patent Application (Art. 97(2) EPC) Dated Feb. 3, 2022 From the European Patent Office Re. Application No. 17855162.8. (4 Pages).

\* cited by examiner

SYSTEMS AND METHODS FOR MINING OF MEDICAL DATA

RELATED APPLICATIONS

This application is a National Phase of PCT Patent Application No. PCT/IL2017/051086 having International filing date of Sep. 27, 2017, which claims the benefit of priority under 35 USC § 119(e) of U.S. Provisional Patent Application No. 62/400,651 filed on Sep. 28, 2016. The contents of the above applications are all incorporated by reference as if fully set forth herein in their entirety.

BACKGROUND

The present invention, in some embodiments thereof, relates to data mining and, more specifically, but not exclusively, to systems and methods for mining of medical data.

The Reference Interval (RI) is a common tool used to interpret the results of clinical tests. The RI represents the normal value range for each analyte. Physicians and other health professionals interpret laboratory tests performed for a certain patient by comparing the test results to the RI for each analyte. Results outside the RI represent abnormal values. Results within the RI represent normal values.

The RI is defined according to one set of guidelines based on tests conducted on 120 healthy subjects. The inner 95% of observed results are defined as the RI, with the limits of the RI set to the lower 2.5% and the upper 2.5% of the result distribution among the healthy subjects.

SUMMARY

According to an aspect of some embodiments of the present invention there is provided a computer implemented method for creating a personalized reference interval (PRI), comprising: receiving a digital profile of a patient, the digital profile including a plurality of demographic parameters and associated values, and the digital profile including medical history data parameters and associated values; receiving a clinical test result of the patient, the clinical test result including a measured value of at least one analyte; accessing a dataset storing a plurality of digital profiles of other patients, each digital profile of the dataset is associated with at least one clinical test result of the respective other patient and the plurality of demographic parameters and associated values for each of the other patients, and medical history data parameters and associated values; identifying a subset of the dataset based a correlation according to a similarity requirement between at least one of the plurality of demographic parameters of the digital profile of the patient and at least one of the plurality of demographic parameters of the digital profiles of the other patients, and based on the correlation according to the similarity requirement between the medical history of the digital profile of the patient and the medical history of the other patients; calculating a personalized reference interval (PRI) for each respective at least one analyte of the clinical test result of the patient according to an analysis of corresponding values of the at least one analyte of the subset, wherein the PRI is dynamically calculated using the most updated version of the dataset; and providing the PRI for each of the at least one analyte of the clinical test result of the patient.

Optionally, the other patients of the subset are designated as healthy and normal, and wherein the PRI denotes a healthy and normal value of the respective analyte for health and normal patients having digital profiles correlated with the digital profile of the patient.

Optionally, the medical history data parameters are indicative of at least one medical pathology.

Optionally, the PRI is calculated to account for contradictory effects of demographics and/or medical history on the respective analyte.

Optionally, the PRI is calculated to account for additive effects of demographics and/or medical history on the respective analyte.

Optionally, the medical history data includes at least one member selected from the group consisting of: past medical history, comorbidity, chronic medical conditions, previous surgeries, current medications, smoking status, alcohol consumption status, drug use status, acute medical conditions, family history, and genetic predisposition.

Optionally, the demographic parameters of the digital profile include one or more members from the group consisting of: age, gender, geographical location, ethnicity, and income.

Optionally, the analyte is measured from a body fluid selected from the group consisting of: blood, urine, cerebrospinal fluid, pleural fluid, amniotic fluid, aqueous humor, vitreous humor, bile, gastric acid, lymph, mucus, pericardial fluid, pus, saliva, semen, vaginal secretions, sputum, synovial fluid, tears, and sweat.

Optionally, the analyte is at least one of: an anatomical body measurement performed directly or using imaging methods, and a measurement of function of an organ. Optionally, the analyte is selected from the group consisting of: body mass index (BMI), cardiac output, respiratory rate, endometrial thickness, appendix size, kidney size, and prostate volume.

Optionally, the digital profiles of the subset include at least one of survival of the respective patient and time to a certain clinical outcome occurring to the respective patient, and further comprising calculating a risk for a certain outcome for the patient according to an analysis of the value of the at least one analyte in view of the PRI. Optionally, the certain outcome is at least one of: received from a user using a graphical user interface (GUI), and determined for each of a list of a plurality of predefined outcomes.

Optionally, the method further comprises receiving at least one another clinical test result of the patient including another measured value of the at least one analyte; determining a trend according to an analysis of difference between the measured value of the at least one analyte of the at least one another clinical test result and the test result; identifying a clinical significance or clinical insignificance of the trend according to the PRI.

Optionally, the digital profiles of the subset include at least one of survival of the respective patient and time to a certain clinical outcome occurring to the respective patient, and wherein the identifying the clinical significance or clinical insignificance of the trend is based on calculating a risk for a certain outcome for the patient based on the trend.

Optionally, the method further comprises identifying the clinical significance or clinical insignificance of the trend based on an analysis of a correlation between the trend and a distribution of values corresponding to the trend in the digital profiles of the subset.

Optionally, the method further comprises storing the received clinical result of the patient and digital profile of the patient in the dataset.

According to an aspect of some embodiments of the present invention there is provided a method of analyzing clinical associations by navigating a dataset of medical data of other patients, comprising: managing a dataset storing a plurality of digital profiles of patients, each digital profile of each patient of the dataset is associated with: a measured value for each of a plurality of analytes obtained during a clinical test of the respective patient, a plurality of demographic parameters for each respective patient, and at least one of survival of the respective patient and time to a certain clinical outcome occurring to the respective patient; receiving, from a graphical user interface (GUI) based on an entry by a user, a certain analyte of the plurality of analytes stored in the dataset; receiving, from the GUI based on an entry by the user, at least one value requirement for at least one of the plurality of demographic parameters of the patients of the dataset, denoting a defined population; receiving, from the GUI based on an entry by the user, a certain outcome; identifying a subset of the plurality of digital profiles of the dataset according to the defined population; instructing a rendering of the GUI to present an association between values of the certain analyte and the certain outcome for the defined population according to the digital profiles of the subset.

Optionally, the certain outcome includes a member selected from the group consisting of: risk of cancer at a predefined future time frame, risk of congestive heart failure at a predefined future time frame, risk of diabetes at a future time frame, risk of liver disease at a predefined future time frame, risk of kidney disease at a predefined future time frame, risk of sepsis at a predefined future time frame, and risk of rehospitalization by a predefined future time frame, risk of all cause mortality at a predefined future time frame, and a value requirement for at least one analyte at a predefined future time frame.

Optionally each of the plurality of digital profiles of the dataset include a value for each of a plurality of medical history data parameters; further comprising receiving, from the GUI based on an entry by the user, a certain at least one of the plurality of medical history data parameters; and wherein the subset is identified according to the a certain at least one of the plurality of medical history data parameters.

Optionally, the medical history data includes at least one member selected from the group consisting of: past medical history, comorbidity, chronic medical conditions, previous surgeries, current medications, smoking status, alcohol consumption status, drug use status, acute medical conditions, family history, and genetic predisposition.

According to an aspect of some embodiments of the present invention there is provided a system for creating a personalized reference interval (PRI), comprising: a data storage device storing a dataset storing a plurality of digital profiles of patients, each digital profile of the dataset is associated with at least one clinical test result of the respective patient and respective values for at least one demographic parameter, each digital profile including medical history data parameters and associated values; a program store storing code; and at least one processing unit coupled to the data storage device and the program store for implementing the stored code, the code comprising: code to receive a digital profile of a patient including at least one demographic parameter and associated value and medical history data parameters and associated values, and to receive a clinical test result of the patient, the clinical test result including a measured value of at least one analyte; code to identify a subset of the dataset based a correlation according to a similarity requirement between at least one of the plurality of demographic parameters of the digital profile of the patient and the at least one of the plurality of demographic parameters of the digital profiles of other patients, and based on the correlation according to the similarity requirement between the medical history of the digital profile of the patient and the medical history of the other patients, and calculate a personalized reference interval (PRI) for each respective at least one analyte of the clinical test result of the patient according to an analysis of corresponding values of the at least one analyte of the subset, wherein the PRI is dynamically calculated using the most updated version of the dataset; and code to provide the PRI for each of the at least one analyte of the clinical test result of the patient.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

The present invention, in some embodiments thereof, relates to data mining and, more specifically, but not exclusively, to systems and methods for mining of medical data.

An aspect of some embodiments of the present invention relates to systems and/or methods (e.g., code instructions executed by a processor(s)) for calculating a personalized reference interval (PRI) for an analyte of a clinical test result of a current patient. The PRI may be used as a tool to compare the value of the analyte of the clinical test of the patient to values of the analyte obtained in tests of other patients having a similar demographic profile and/or similar medical background.

The PRI may be used to improve the ability to determine the clinical significance of the measured value of the analyte of the patient (obtained by the clinical test). The PRI provides a comparison of the analyte value of the current patient with analyte values associated with other patients that are similar to the current patient, rather than, for example, a comparison based on patients that are different than the current patient in terms of demographic profile and/or medical background.

The PRI is calculated by identifying a subset of patients having demographic parameter value(s) that correlate (e.g., according to a similarity requirement) with demographic parameter value(s) of the current patient. The correlation improves selection of patients having a similar demographic background to the current patient. The PRI is calculated for each analyte measured by the clinical test for the certain patient, by analyzing the corresponding values of the analyte of the identified subset of patients.

The PRI may be calculated using data obtained from subjects designated as normal and/or healthy. Such a PRI may be used as a tool for comparison between the analyte value of the certain patient with normal and/or healthy subjects of a similar demographic profile to the demographic profile of the certain subject, for example, patients of a similar age, gender, and/or income. Alternatively or additionally, the PRI may be calculated using data obtained from subjects having a similar (e.g., according to a similarity requirement) medical history to the medical history of the current subject, for example, patients taking similar medications, having similar comorbidities, and/or a similar smoking history.

Optionally, a risk of clinical outcome (e.g., hazard ratio and/or a relative risk) is calculated for a certain outcome for the certain patient according to an analysis of the analyte value in view of the PRI. The risk is calculated based on data stored in association with the dataset indicative of survival of the respective subject of the dataset and/or time for a certain clinical outcome to occur to the respective subject of the dataset.

Optionally, a trend is calculated based on multiple sequentially obtained values for the analytes, for example, obtained by repeat testing separated by time periods (e.g., once a month, or once a day, or once a year). The trend is based on differences and/or changes to the value for the common analyte for the multiple tests.

The trend may be analyzed to detect whether the trend represents a clinically significance event, or is not of clinical significance. The trend may be analyzed in view of a distribution of values in the digital profiles of the subset of the dataset.

An aspect of some embodiments of the present invention relates to systems and/or methods (e.g., code instructions executed by a processor(s)) that create instructions for rendering a graphical user interface (GUI) that presents an association between values of a certain analyte, and a certain outcome for a defined population, for example, as a graph or chart. The associations are calculated based on digital profiles of patients stored in a dataset. The dataset stores test results (i.e., measured values for the analyte) obtained for patients, clinical outcomes for the patients, and/or demographic and/or medical history data for the patients. The user may use the GUI to enter and/or select the certain analyze, the certain outcome, and parameter(s) that define the defined population. The associations are dynamically calculated using the data stored in the dataset, which may help the user discover new associations, and/or evaluate variations of known associations.

The systems and/or methods described herein improve an underlying technical process within the technical field of comparison of medical test results. The systems and/or methods described herein improve the process of accurately comparing measured test values from one patient to measured test values of other patients, by improving the process of selecting the other patients that most closely resemble the current patient, for example, in terms of similar demographics, and/or similar medical background. The technical improvement lies in the dynamic calculation of the PRI based on the most current patient data, taking into account contradictory and/or additive effects of demographics and/or medical history.

The systems and/or methods described herein (e.g., PRI generation code executed by one or more processors) address the technical problem of data mining to select the data that is most significant (e.g., highest correlation) to personalized data of a patient, which has real-world significance. The systems and/or methods described herein improve the process of determining whether a measured test result is of clinical significance or clinical insignificance, by providing a more accurate comparison. For example, the hemoglobin level of patients with sickle cell disease is normally lower than the hemoglobin level of healthy patient without sickle cell disease.

The systems and/or methods described herein generate the PRI, which may be used to compare the against "normal" hemoglobin levels of patients with sickle cell disease, rather than comparing against "abnormal" healthy patients without sickle cell disease. In another example, mineral bone density values are generally lower for older women relative to younger women. In yet another example, certain medications may affect analyte values as a side effect, to values outside of the "normal" range. Such side effects are to be expected (i.e., "normal") outcomes.

The systems and/or methods described herein calculate the PRI in cases in which the patient has multiple medical pathologies and/or medical conditions that provide contradictory effects on analyte(s). For example, as discussed above, patients with sickle cell anemia generally have normally lower hemoglobin levels than patients without sickle cell anemia. Patients living at high altitude (or visiting high altitude locations) generally have a higher hemoglobin level than patients living at low altitudes. The systems and/or methods described herein calculate the PRI for a patient that accounts for the contradictory effects of sickle cell anemia and living at a high altitude.

The systems and/or methods described herein calculate the PRI in cases in which the patient has multiple medical pathologies and/or medical conditions that provide additive effects on analyte(s). For example, as discussed above, patients with sickle cell anemia generally have normally lower hemoglobin levels than patients without sickle cell anemia. Patients that have low iron intake may experience iron deficiency anemia, resulting in a lower hemoglobin level than patients with such anemia. The systems and/or methods described herein calculate the PRI for a patient that accounts for the additive effect of sickle cell anemia and iron deficiency anemia.

The systems and/or methods described herein calculate the PRI for patients with complex medical histories and/or demographic profiles, for which determining the normal range of the RI of the respective analyte is difficult and/or not obvious, due to contradictory and/or additive effects of the complex medical history and/or demographic profile.

The systems and/or methods described herein address the technical problem of providing easy (or improving) user navigation of medical data in a dataset of a large number of patients, to identify clinically significant associations between tests results and clinical outcomes (e.g., survival, development of a medical condition) for a certain patient population defined by demographic and/or medical history. The large number of possible permutations and/or combinations of the medical data and/or test results may hide clinically significant associations. The systems and/or methods described herein provide an interactive GUI that navigates the dataset according to user inputs (optionally entered in real-time), such as the user entering one or more values for parameters. The GUI is presented on a physical user interface, such as a display, optionally a touch-screen. The user enters data using a physical user interface, which may be the touch-screen, or a keyboard, mouse, or other physical device.

The systems and/or methods described herein improve performance of the computing unit executing the PRI generation code, and/or other code instructions described herein. The improvement in performance is obtained by reducing the processing time, processing resources, and/or memory resources to create the PRI.

For example, manual methods used by a user may be used to look up the medical history and/or demographic profile of the user, and for each medical condition and/or demographic profile of the user, look up in the medical literature effects of the medical condition to determine whether the test value is of clinical significance or not, i.e., whether the test value is "normal" for the patient with the associated demographic parameters and/or medical parameters, or "abnormal". The systems and/or methods generate the PRI for patients with complex medical background, for example, having multiple chronic illnesses, taking medications which may affect values of rest results, and of a certain demographic profile. For such patients, the systems and/or methods described herein generate the PRI to help the user determine whether the test results are clinically significant (i.e., abnormal) or clinically insignificant (i.e. normal), while other methods may not be able to determine what is "normal", and may rely on guesses by the physicians, which are prone to medical error.

In another example, the GUI provides functions to the user to navigate the large dataset to identify clinically significant associations between an analyte and one or more clinical outcomes for a defined population (e.g., according to demographics and/or medical history) provides improved computational efficiency in finding the clinically significant associations by improved targeting and/or organization of the underlying data.

For example, the GUI provides a function to the user to select the parameters to define the population, select the clinical outcomes, and/or select the analyte(s), which provides for improved computational efficiency in identifying, sorting, and presenting the relevant data for visual analysis by the user.

The systems and/or methods described herein may improve performance of a computing system, such as a client terminal, network, and/or network server, for example, by reducing processor utilization, reducing data traffic over the network, and/or by reducing storage requirements. Improvements may occur, for example, by the user using the GUI to view different associations between analytes and clinical outcome(s) for a certain patient population, optionally according to real-time user entered data, in comparison to, for example, a brute force method and/or manual method that sequentially or blindly analyzes a large number of combinations and/or permutations of the data to attempt to identify an association, which may or may not be clinically relevant.

The systems and/or methods described herein may generate new data (which may be presented to the user on the GUI, stored, and/or transmitted to another server) that include the PRI. The PRI is created as customized data for the patient, which may be used by users (e.g., clinicians) to determine whether a test result for a certain analyte is clinically significant or not. The GUI described herein presents associations in clear real-world terms to the user, to help the user determine whether the association is clinically significant or not.

The systems and/or methods described herein provide a unique, particular, and advanced technique of customizing data from a large number of patients to a certain patient, and/or to provide an interview to a user to view associations to identify clinically significant associations.

Accordingly, the systems and/or methods described herein are inextricably tied to computer technology, to overcome an actual technical problem arising in large datasets, to help identify data that may be used by a user to determine whether a test result is clinically significant or not.

Before explaining at least one embodiment of the invention in detail, it is to be understood that the invention is not necessarily limited in its application to the details of construction and the arrangement of the components and/or methods set forth in the following description and/or illustrated in the drawings and/or the Examples.

The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term clinically significant means whether a test result is associated with a real noticeable effect on the patient that may be effectively treated.

Abnormal test results (i.e., compared to a healthy population) may not be clinically significant if they are due to a long term chronic medical condition that cannot be cured, but is being managed effectively. For example, patients with sickle cell disease have abnormally low hemoglobin level as their "normal" baseline, even when the disease is managed, representing a clinically insignificant event, since the hemoglobin cannot be practically increased.

The systems and/or methods (e.g., code instructions executed by processor(s)) described herein improve accuracy of interpretation of test results (i.e., value(s) of analyte(s)) and/or improve the ability to determine clinical significant of the test results, by using data from a large patient population, rather than, for example, a small number of patients tested by the test manufacturer.

Figure 1:
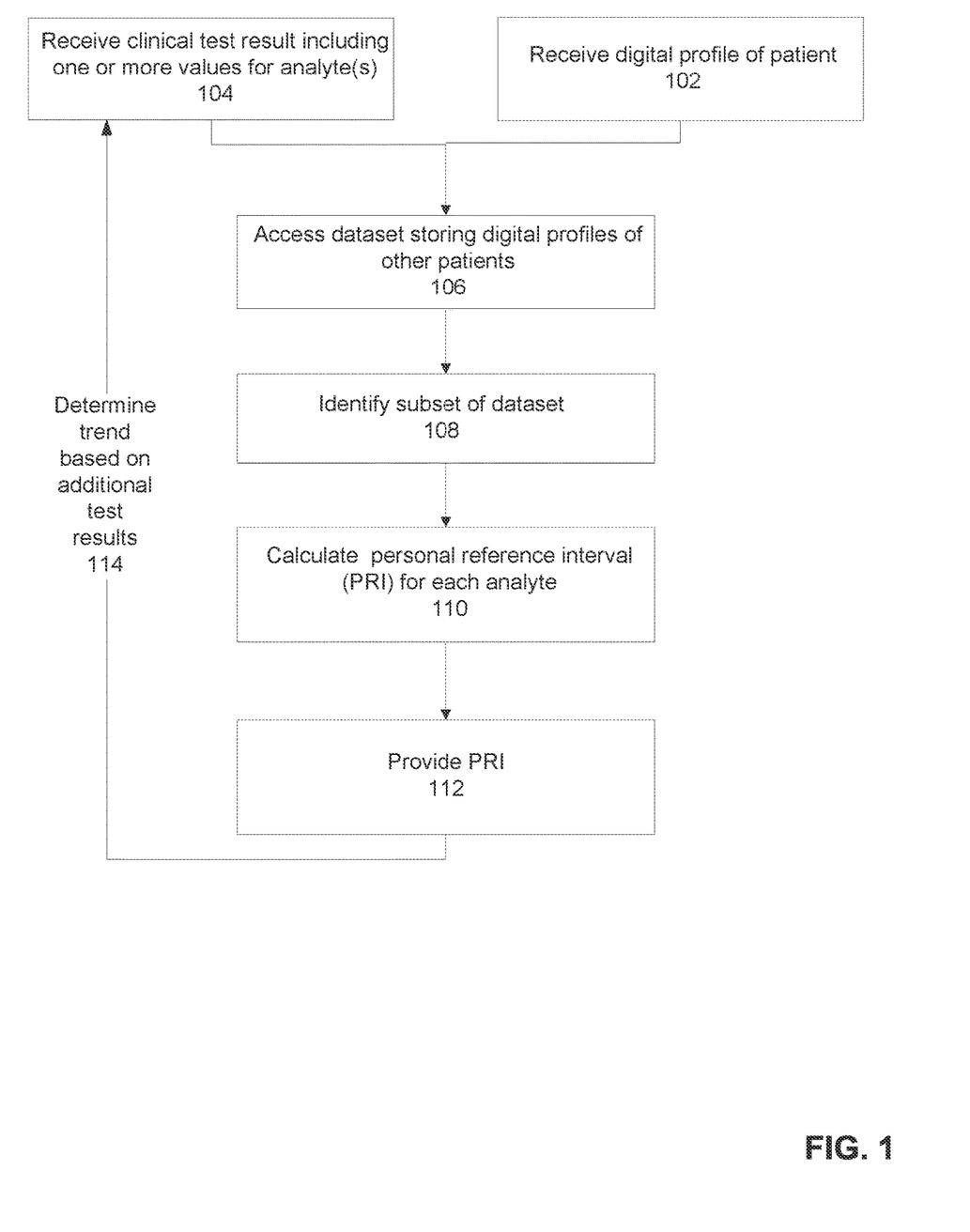
FIG. 1 is a flowchart of a method for creating a personalized RI, in accordance with some embodiments of the present invention.
Figure 2:
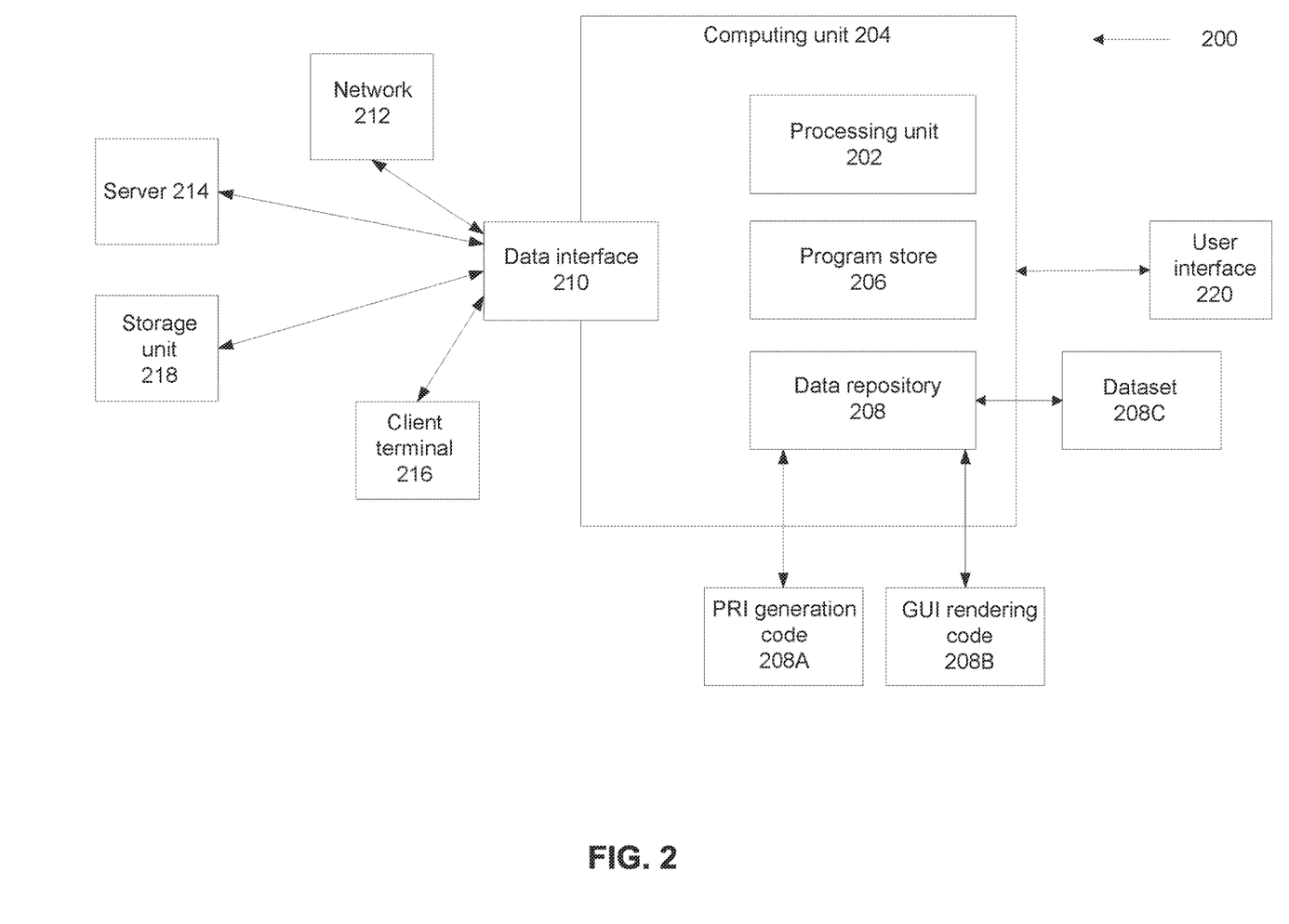
FIG. 2 is a block diagram of components of a system that presents and/or receives a value for an analyte (obtained as part of a clinical test) in view of the PRI, in accordance with some embodiments of the present invention.

Reference is now made to FIG. 1, which is a flowchart of a method for creating a personalized PRI, in accordance with some embodiments of the present invention. Reference is also made to FIG. 2, which is a block diagram of components of a system 200 that provides an interface to a user to enter and/or view a value for an analyte (obtained as part of a clinical test) in view of the PRI, in accordance with some embodiments of the present invention. System 200 may execute the acts of the method described with reference to FIG. 1, for example, by a processing unit 202 of a computing unit 204 executing code instructions stored in a program store 206.

Computing unit 204 may be implemented as, for example, a client terminal, a server, a computing cloud, a web server, a mobile device, a desktop computer, a thin client, a Smartphone, a Tablet computer, a laptop computer, a wearable computer, glasses computer, and a watch computer. Computing unit 204 may include locally stored software that performed one or more of the acts described with reference to FIG. 1, and/or may act as one or more servers (e.g., network server, web server, a computing cloud) that provides services (e.g., one or more of the acts described with reference to FIG. 1) to one or more client terminals, for example, providing software as a service (SaaS) to the client terminal(s), providing an application for local download to the client terminal(s), and/or providing functions using a remote access session to the client terminals, such as through a web browser. For clarity, computing unit 204 is shown as a single component, but it is understood that computing unit 204 may be implemented using other architectures, such as the client-server design.

Processing unit 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processing unit(s) 202 may include one or more processors (homogenous or heterogeneous), which may be arranged for parallel processing, as clusters and/or as one or more multi core processing units.

Program store 206 stores code instructions implementable by processing unit 206, for example, a random access memory (RAM), read-only memory (ROM), and/or a storage device, for example, non-volatile memory, magnetic media, semiconductor memory devices, hard drive, removable storage, and optical media (e.g., DVD, CD-ROM).

Computing unit 204 may include a data repository 208 for storing data, for example, PRI generation code 208A (that performs one or more acts of the methods described with reference to FIG. 1), and/or GUI rendering code 208B (that creates instructions for rendering the GUI, as described herein), and/or dataset 208C (that stores patient data, as described herein). Data repository 208 may be implemented as, for example, a memory, a local hard-drive, a removable storage unit, an optical disk, a storage device, and/or as a remote server and/or computing cloud (e.g., accessed using a network connection).

Dataset 208C may be represented as, for example, electronic medical records (e.g., according to a predefined standard), a database of records, and a table where each column stores a value for a respective parameter. It is noted that dataset 208C may be implemented as a single dataset, or a distributed dataset, dynamically organized from different tables and/or other different dataset (e.g., stored locally on a computing unit, provided by a client terminal, and/or stored remotely on one or more remote servers). The PRI may be dynamically created by selection of relevant parameters from the common dataset, and/or from the distributed tables.

Computing unit 204 may include a data interface 210, for example, one or more of, a network interface card, a universal serial bus (USB) connector, a wireless interface to connect to a wireless network and/or storage device, a physical interface for connecting to a cable for network connectivity, a virtual interface implemented in software, network communication software providing higher layers of network connectivity, and/or other implementations.

Computing unit 204 may connect using data interface 210 and/or network 212 (and/or another communication channel, such as through a direct link (e.g., cable, wireless) and/or indirect link (e.g., via an intermediary computing unit such as a server, and/or via a storage device) with one or more of: a server(s) 214 (e.g., which may be used to access additional patient data, and/or provide remote services), client terminal 216 (e.g., when computing unit 204 acts as a server, for example, providing SaaS), and a storage unit 218 (e.g., a storage server, a computing cloud storage server, which may store dataset 208C or portions thereof).

Computing unit 204 includes or is in communication with a user interface 220 that provides a user with a mechanism to enter data and/or view presented data.

Exemplary user interfaces 220 include, for example, one or more of, a touchscreen, a display, a keyboard, a mouse, and voice activated software using speakers and microphone.

At 102, a digital profile of a patient (referred to herein as the current patient, or the certain patient, to differentiate from the other patients and/or subjects having data stored in the dataset) is received by computing unit 204. The profile may be manually entered by a user (e.g., using user interface 220, and/or client terminal 216), obtained from storage (e.g., accessing server 214 that stores a medical record of the patient), and/or stored within dataset 208C and/or other implementations.

The digital profile may be implemented, for example, as a record(s), database entry (or entries), and/or values assigned to a set of parameters. The digital profile may be implemented as an electronic medical record, for example, based on existing electronic medical records of the patient.

The digital profile includes a set of demographic parameters and associated values for the patient. Exemplary demographic parameters of the digital profile include one or more: age, gender, geographical location, ethnicity, and income. The demographic parameters may be selected, for example, based on demographic parameters associated with determinants of health, public health associated demographic factors, and/or based on available data.

Alternatively or additionally, digital profile includes additional medical history data (also referred to herein as a medical profile) of the patient, for example, data obtained from medical record(s) of the patient. Exemplary medical history data includes one or more of: past medical history, comorbidity, chronic medical conditions, previous surgeries, previous treatments (e.g., chemotherapy, radiation therapy), current medications, previous medications, smoking status, alcohol consumption status, drug use status, acute medical conditions, family history, and genetic predisposition to certain clinical outcomes.

At 104, a clinical test result of the patient is received by computing unit 204. The clinical test result includes measured value(s) of one or more analytes. The clinical test result may be manually entered by a user, retrieved from storage (e.g., from the medical record of the patient), and/or provided by another computing unit (e.g., provided by a server of the laboratory that conducted the measurements on the sample used for testing).

It is noted that blocks 102 and 104 may occur in parallel and/or simultaneously, for example, the clinical test result is provided as part of the digital profile of the patient.

Exemplary clinical tests include: a blood test performed on a blood sample, urine analysis performed on a urine sample, or analysis of another fluid obtained by invasive or non-invasive methods. Optionally, the analyte is measured from a body fluid sample, for example, blood, urine, cerebrospinal fluid, pleural fluid, amniotic fluid, aqueous humor, vitreous humor, bile, gastric acid, lymph, mucus, pericardial fluid, pus, saliva, semen, vaginal secretions, sputum, synovial fluid, tears, and sweat.

The analyte may include a measurement (e.g., concentration) of a substance, for example, ions (e.g., calcium, iron, chlorine), proteins (e.g., albumin, creatinine), enzymes (AST, ALT), human cells (e.g., red blood cells, white blood cells), organisms (e.g., bacteria, fungus, viruses), foreign substances (e.g., lead), and/or other substances found in the body (i.e., endogenous or exogenous).

Alternatively or additionally, the analyte includes an anatomical body measurement performed directly (e.g., using a ruler) and/or using imaging methods (e.g., measured on an x-ray, a CT scan, using an ultrasound machine), for example, body mass index (BMI), head circumference, endometrial thickness, appendix size, kidney size, and prostate volume.

Alternatively or additionally, the analyte includes a measurement of function of an organ, for example, cardiac output, total lung capacity, residual volume, and urine output.

It is noted that as used herein, the term analyte may sometimes include additional measures obtained from the patient, not necessarily based on chemical constituents.

Optionally, the data of the clinical test is added to the digital profile of the current patient and stored in dataset 208C. Adding the test results (for which the PRI is calculated) to the dataset increases the number of tests results associated with digital profiles of patients, which improves the accuracy of the PRI calculated for other patients.

At 106, dataset (e.g., 208C) storing digital profiles of other patients is accessed and/or managed by computing unit 204. Each digital profile of each patient of the dataset is associated with clinical test result(s) that includes values of each patient obtained during clinical tests for the analyte of the clinical test of the patient being analyzed (i.e., as described with reference to block 104). For example, when the clinical test of the patient includes Hemoglobin, the Hemoglobin levels of other patients of the dataset are accessed, as described herein.

It is noted that in practice, the digital profiles may be missing information, such that every digital profile of every patient does not necessary contain values for all parameters. In such cases, the analysis described herein is performed with the information that is available. Profiles with missing information may be used with the existing information, or excluded from the analysis.

The digital profiles of the other patients of the dataset include the demographic parameters associated with the current patient. The current patient may be an entry within dataset 208C, which is based on a similar structure to the entries of the other patients, for example, an electronic medical record based on a common format.

Optionally, the digital profiles of the other patients of the dataset include the additional medical history data associated with the current patient.

Optionally, the digital profiles of the other patients include a survival of the respective patient, for example, how long the patient lived (i.e., age at death), and/or how long the patient lived after being diagnosed with a medical condition (e.g., how many years the patient survived after being diagnosed with cancer). Alternatively or additionally, the digital profiles of the other patients include time to a certain event occurring to the respective patient (also referred to herein as a clinical outcome, or outcome), for example, time for readmission to a hospital after a previous discharge in a patient with congestive heart failure, time to develop cancer in a 60 year old patient, and time to develop an infection in a joint prosthesis in a patient operated on for osteoarthritis of the knee.

Optionally, a user selects one or more outcomes (e.g., from the different outcomes defined for the patients of the dataset) for analysis. The selection may be performed with reference to block 102, together with the test result, and/or independently of the test result, when the test result is received, or before and/or after the test result is received. The clinical outcome may be selected using the GUI presented on a display of client terminal 216, of computing unit 204, and/or using user interface 220 or another interface. The user may manually enter the desired outcome (e.g., using key words entered into a field) and/or select from a list of defined outcomes (e.g., clicking a check box next to each outcome, or clicking the outcomes).

At 108, a subset of the dataset (i.e., a subset of user profiles) is identified by computing unit 204 (e.g., processing unit 202 executing PRI generation code 208A stored in program store 206 and/or data repository 208).

The subset is identified based a correlation between the digital profile of the patient and the digital profiles of other patients. The correlation is performed at least according to selected demographic parameters and/or selected medical history parameters of the digital profile of the patient and the digital profiles of the other patients. The demographic parameters and/or the medical history parameters used for the correlation may be selected by the user using the GUI.

The correlation is defined according to according to a similarity requirement that represents a desired amount of similarity between the profiles of the current patient and other patients. The portions of the digital profile used to identify the subset may include the demographic parameters and/or the medical history parameters, and/or based on user input. All parameters of the digital profile may be used in determining the subset, or a selected subset of parameters.

The user may use the GUI to select the parameters of the digital profile to be used in determining the correlation for identification of the subset. The user may assign weights to the parameters, for example, when a weighted function is used to determine the correlation.

The similarity requirement may be implemented, for example, as a threshold (e.g., select profiles above a predefined value), a range (e.g., select profiles within a range of values), a function, (e.g., select profiles that meet a certain condition), and/or a relative relationship (e.g., select the top 10 profiles).

The similarity requirement may be calculated using a correlation function, a distance function, or other statistical analysis method. For example, a weighted function that calculates a correlation between each profile and the profile of the current patient, and/or a statistical distance function that calculates a statistical distance between a vector representation of each digital profile and the vector representation of the digital profile of the current patient. Different parameters may be assigned different weights. For example, age may be assigned a larger weight than geographical location.

Optionally, the identification of the subset is designated to include patients of the subset that are designated as healthy and normal, for example, based on a healthy and/or normal flag field in the digital profile. The healthy and/or normal patients may be selected by excluding digital profiles of patients taking medications and/or having one or more chronic illnesses. The healthy and/or normal patients may be selected when the current patient is usually healthy and/or normal (e.g., no chronic illnesses or long term medication use). In this manner, the PRI may be generated based on demographics.

Alternatively, the identification of the subset is designed to include patients of the subset that have a similar medical history (e.g., medical profile) as the patient, according to the similarity requirement. For example, the similarity requirement may be defined categorically. For example, when the patient has stage 3 prostate cancer, the similarity requirement may be defined to include one or more of: other patients with stage 3 prostate cancer, other patients with any stage of prostate cancer, other patients with any cancer, and other patients with previously treated prostate cancer. In this manner, the PRI may be generated based on patients with a similar medical background.

At 110, the PRI is calculated, optionally by PRI generation code 208A executed by processing unit 202 of computing unit 204. The PRI may be automatically calculated for each analyte of the clinical test result of the patient, and/or calculated for user selected analytes. For example, the user may use the GUI to select the analytes for which the PRI is calculated.

The PRI is calculated based on data associated with the identified subset of digital user profiles of the dataset, using corresponding values of the analyte.

For example, for hemoglobin level, the PRI is calculated using hemoglobin values of the identified subset.

Optionally, the PRI is calculated to account for contradictory effects of demographics and/or medical history on the respective analyte, by providing a single unified measure that takes into account the contradictory effects on the respective analyte for the current user, for example, the contradictory effects of sickle cell anemia and residing at a high geographical altitude, as described herein.

Alternatively or additionally, the PRI is calculated to account for additive effects of demographics and/or medical history of the respective analyte, by providing a single unified measure that takes into account the additive effects on the respective analyte for the current use. For example, the additive effect in reducing bone density due to old age and steroid based medications.

The PRI may be calculated using one or more of the following exemplary methods:

Average of the analyte values based on the subset of digital profiles.

Distribution of the analyte values, and/or standard distribution of the analyte values.

Range representing 95% of the analyte values, starting at the bottom 2.5% and ending at the top 2.5%.

The PRI provides a comparison tool for evaluation of the value of the analyte of the current patient, by comparing with a large number of patients (which may be larger than the sample size required by manufacturers to generate standard RI), by comparing with patients of a similar demographic profile, and/or by comparing with patients of a similar medical profile. The PRI provides a more accurate indication of whether the analyte value of the test result of the current patients is representing an underlying clinically significant event (which may require further investigation and/or treatment), or does not represent a clinically significant event (no further investigation and/or treatment is to be pursued). The PRI assisting the physician (or other user) in determining whether the analyte value is normal or abnormal personalized for the current patient. For example, using the PRI, a physician may detect that a certain analyte, which would otherwise be abnormal for a patient with a complex medical history, is normal, and no further treatment or investigation is warranted. In another example, using the PRI, the physician may detect that the certain analyte, which would otherwise be normal, is actually abnormal for a patient with the complex medical history, and additional treatment and/or investigation is required.

Optionally, a risk (e.g., hazard ratio and/or a relative risk) is calculated for the certain outcome (which may be entered by the patient using the GUI) according to an analysis of the value of the analyte in view of the PRI. The risk may be calculated based on the survival time data and/or time to event data associated with the digital profiles of the patients of the identified subset.

Optionally, the PRI is dynamically created during runtime, based on the most current data within the dataset 208C. Block 106 may be executed in real time when the clinical test result is received to access the most updated version of dataset 208C.

The identification of the subset (as described with reference to block 108) may be performed in real time.

At 112, the PRI is provided for each (or selected) of the analytes of the clinical test result of the patient.

The PRI may be represented as a single number, a range, a distribution, and/or other representations. The PRI may be presented (e.g., on the GUI) as a number, as a range of numbers as a line (which may include the relative location of the value of the analyte of the patient with or outside the line), and/or as a graph showing the distribution (e.g., bar graph).

A report may be presented using the GUI, graphically and/or numerically depicting the relative relationship between the analyte value of the result of the current patient and the PRI.

The PRI may be stored, for example, in the medical record of the patient. The PRI may be used for subsequent tests, and/or used to evaluate trends, as described herein. The PRI may be updated with new data of other patients when the new data is added to the dataset.

Optionally, at 114, one or more additional clinical test results of the patient are received. The additional tests include additional measured value(s) of the one or more analytes for which the PRI has been generated. For example, the patient may undergo repeated tests to monitor the medical condition on a regular basis, for example, measurements of Hemoglobin A1C once every three months to evaluate glucose control in diabetics. In another example, the patient may undergo a test to evaluate the same analyte, but for a different medical indication.

A trend is determined according to an analysis of the difference between the measured value of the analyte of the most recent test and the analyte of the previous test. The differences may be calculated sequentially, between the most recent tests, and/or between the most recent test and the earliest test, or other tests.

A clinical significance or clinical insignificance of the trend is identified according to the generated PRI. Clinical significance of the trend may be indicated by motion of the value of the analyte out of the PRI. For example, when values of a first test falls within the PRI, followed by a second value that is higher, but still within the PRI, followed by third and fourth values that sequentially increase and are out of the PRI, may be suggestive of clinical significance. Clinical insignificance of the trend may be indicated when the values of the analyte remain within the PRI, such as in cases in which the value moves but remains within the PRI. The PRI may distinguish between cases in which motion of the analyte value moves out of a standard RI (i.e., based on normal healthy subjects), but remains within the PRI, which may be more accurate of clinical insignificance of the motion of the analyte value for the current patient.

The clinical significance or clinical insignificance of the trend may be identified based on an analysis of a correlation between the trend and a distribution of values corresponding to the trend in the digital profiles of the subset. The correlation may be calculated, for example, by considering the set of values obtained by sequential testing as a vector (for each digital profile), and calculating a statistical distance between the vectors. The statistical distance may help determine whether the motion pattern of the analyte is typical for patients with similar demographics and/or medical backgrounds. For example, the analysis may determine that blood calcium levels rise slowly over time in patients with cancer, which may be indicative of clinical insignificance and no further investigation may be necessary. In another example, the analysis may determine that rising and falling values pattern of a certain analyte, which may remain within the PRI, may actually represent an abnormal pattern and may be clinically significant, since for similar patients the values remain stable.

Optionally, the clinical significance or clinical insignificance of the trend is identified based on calculating a risk (e.g., hazard ratio and/or relative risk) for a certain outcome for the patient.

The risk may be evaluated using a risk requirement, for example, a threshold or range that defines when the risk represents a clinical significant trend or clinical insignificant trend. For example, the trend of increasing values of a certain analyte may be associated with a risk of 3 for death from heart disease (which may be clinically significant), while a trend of decreasing values or stable values of the certain analyte may be associated with a risk of 1.5 for death from heart disease (which may be clinically insignificant). The risk for the trend may be calculated using the survival data of the patients of the subset and/or time to the clinical outcome of the patients of the subset.

Figure 3:
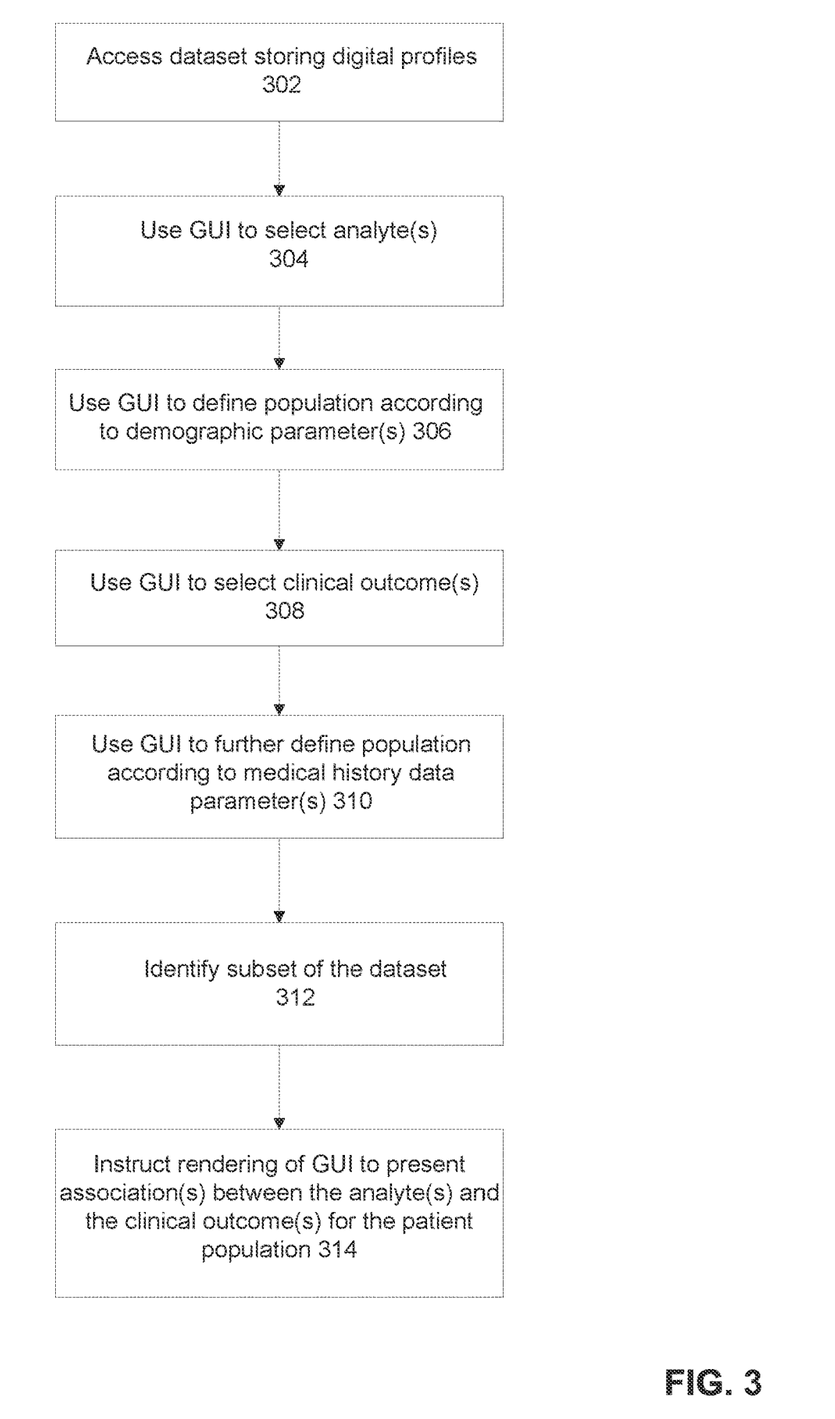
FIG. 3 is a method of analyzing clinical test results by navigating a dataset of medical data of other patients, in accordance with some embodiments of the present invention.

Reference is now made to FIG. 3, which is a method of analyzing clinical test results by navigating a dataset of medical data of other patients, in accordance with some embodiments of the present invention. The method described with reference to FIG. 3 creates the GUI which graphically presents associations between values of one or more analytes and one or more clinical outcomes for a defined patient population. The method described with reference to FIG. 3 may be executed by system 200, for example, GUI rendering code 208B (stored in program store 206 and/or data repository 208) executed by processing unit 202 of computing unit 204. The GUI may be presented on a display of the client terminal used by the user, for example, within a web browser, or another application.

At 302, dataset 208C is accessed. Dataset 208C stores digital profiles of patients. Each digital profile of each patient of the dataset is associated with: a measured value for each analyte obtained during a clinical test for the respective patient, values for demographic parameters for each respective patient, and survival of the respective patient and/or time to a certain clinical outcome occurring to the respective patient.

At 304, one or more analytes are selected by the user using the GUI, for example, by manually entering keywords describing the analyte, and/or selecting the analyte(s) from a list of available analytes.

At 306, a population is defined by the user using the GUI. The user may define the population according to value(s) for one or more demographic parameters of the patients of the dataset. For example, the user may enter an age range for the age parameter, and select male and/or female for the gender parameter.

At 308, one or more clinical outcomes are selected by the use using the GUI. Exemplary clinical outcomes include: risk of cancer at a predefined future time frame, risk of congestive heart failure at a predefined future time frame, risk of diabetes at a future time frame, risk of liver disease at a predefined future time frame, risk of kidney disease at a predefined future time frame, risk of sepsis at a predefined future time frame, and risk of rehospitalization by a predefined future time frame, and risk of all cause mortality at a predefined future time frame, and a value requirement (e.g., threshold, range) for at least one analyte at a predefined future time frame (which may be a different analyte than the selected analyte).

The specific types of disease, such as cancer, may be selected.

The predefined future time frame may be selected, for example, 5 years, 10 years, or other values.

Optionally, at 310, additional medical history data parameters are defined by the user using the GUI. The user may define the medical history of the population according to value(s) for one or more medical history parameters of the patients of the dataset.

The defined population may include the selected medical history parameter(s) and/or the selected demographic parameter(s).

Exemplary additional medical history parameters that may be used to define the population include: past medical history, comorbidity, chronic medical conditions, previous surgeries, current medications, smoking status, alcohol consumption status, drug use status, acute medical conditions, family history, and genetic predisposition.

At 312, a subset of the digital profiles of the dataset is identified according to the defined population, based on the similarity requirement, as described herein.

At 314 GUI rendering code 208B instructs a rendering of the GUI to present an association(s) between values of the selected analyte(s) and the selected clinical outcome(s) for the defined population using the data of the digital profiles of the datasets correlated with the parameters of the defined population (e.g., according to the similarity requirement).

Exemplary associations presented by the GUI include:

Association between ALT values (i.e., analyte) and 5 year mortality risk (i.e., outcome) in males age 40-50 (i.e., population).

Association between BMI (i.e., analyte) and 1 year hospitalization due to a cardiology related condition (i.e., outcome) in females age 60-70 taking hormone replacement therapy (i.e., population).

Association between uric acid values (i.e., analyte) and 10 year prostate cancer incidence risk (i.e., outcome) in males age 60-70.

Figure 4A:
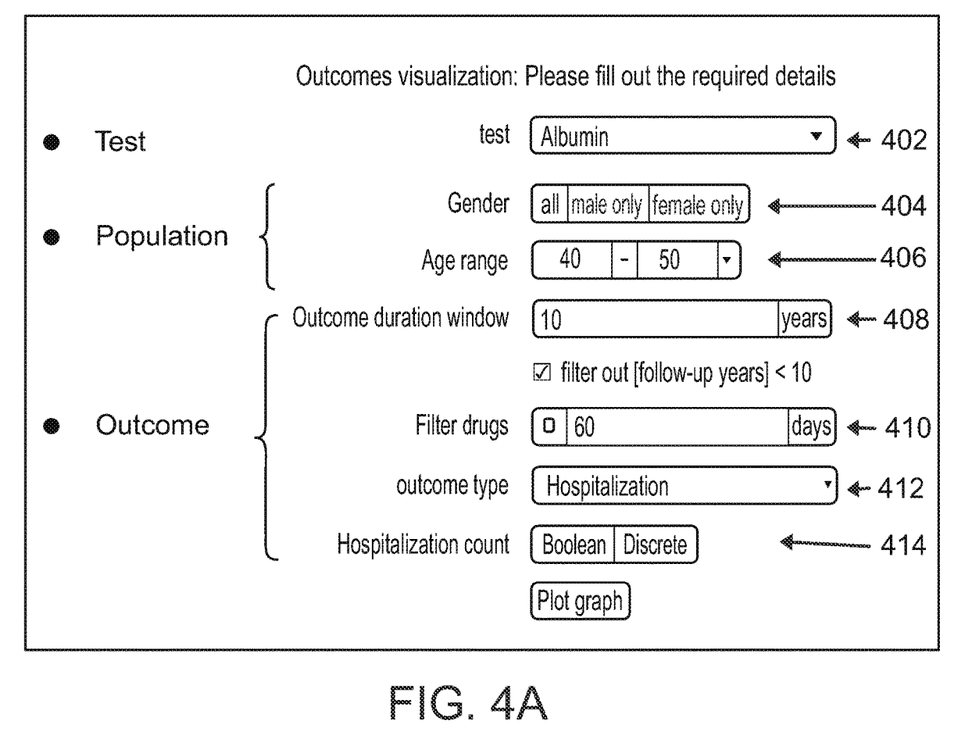
FIGS. 4A-4B are screen captures of an exemplary GUI to navigate associations based on data stored in digital profiles of a dataset, in accordance with some embodiments of the present invention.
Figure 4B:
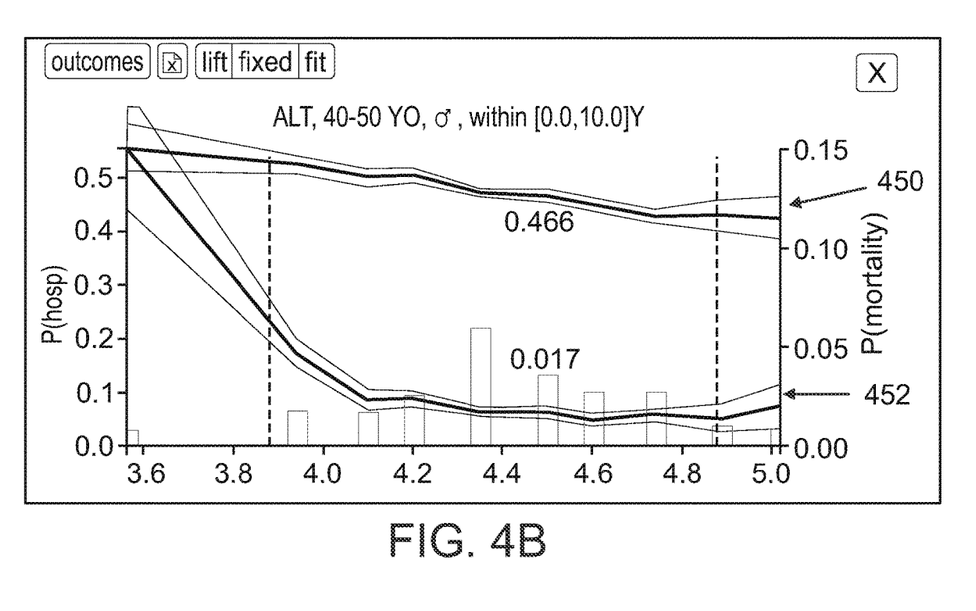

Reference is now made to FIGS. 4A-4B, which are screen captures of an exemplary GUI to navigate associations based on data stored in digital profiles of a dataset, in accordance with some embodiments of the present invention. The screen captures of FIGS. 4A-4B may be created according to the method described with reference to FIG. 3, optionally implemented using system 200 described with reference to FIG. 2, optionally according to instructions described with reference to FIG. 1.

FIG. 4A is a screen capture of an exemplary GUI in which Albumin is selected as the test analyte 402. The population is defined according to a selection of male only based on gender 404, and 40-50 for age range 406. The outcome is defined by a 10 year outcome 408 (with selection to filter out those having a follow up of less than 10 years). No drugs have been selected for filter drugs 410. Hospitalization is selected as outcome type 412. Hospitalization counts 414 are selected as Boolean.

Field 402 denotes the analyte (i.e., test). Fields 404-406 denotes the defined population. Fields 408-414 denote the clinical outcome.

FIG. 4B is a screen capture of a graph based on the selections using the GUI of FIG. 4A. Graph 450 depicts an association between values of Albumin (i.e., analyte) and 10 year all cause hospitalization risk (i.e., outcome) in males age 40-50 (i.e., defined population). Graph 452 depicts an association between values of Albumin (i.e., analyte) and 10 year all cause mortality (i.e., outcome) in males age 40-50 (i.e., defined population).

Figure 5A:
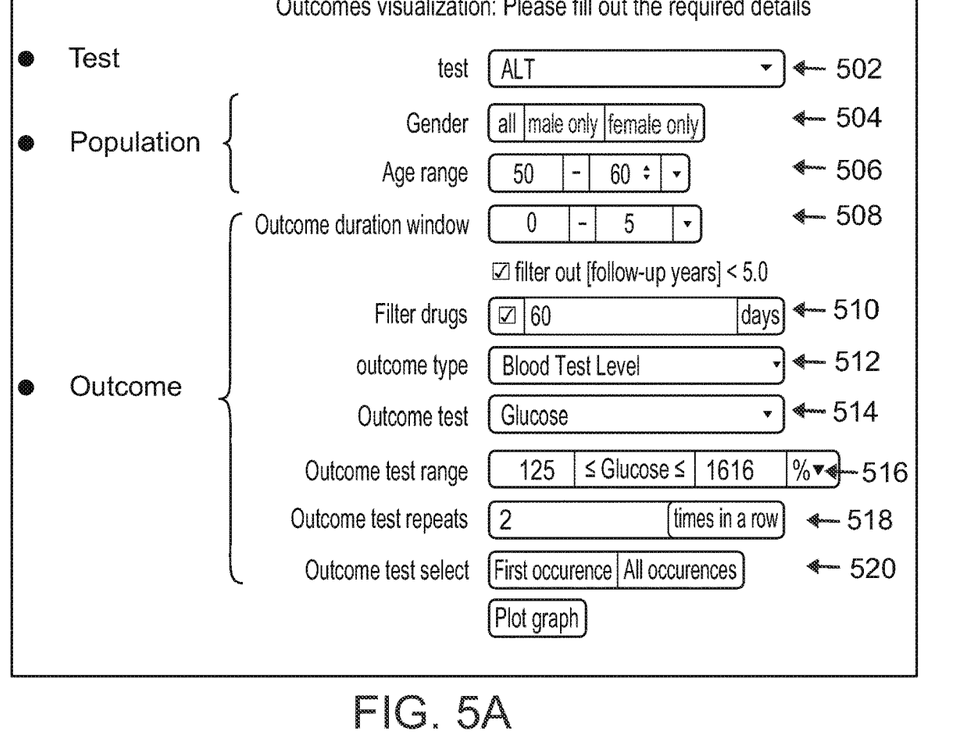
FIGS. 5A-5B are screen captures of another exemplary GUI to navigate associations based on data stored in digital profiles of a dataset, in accordance with some embodiments of the present invention.
Figure 5B:
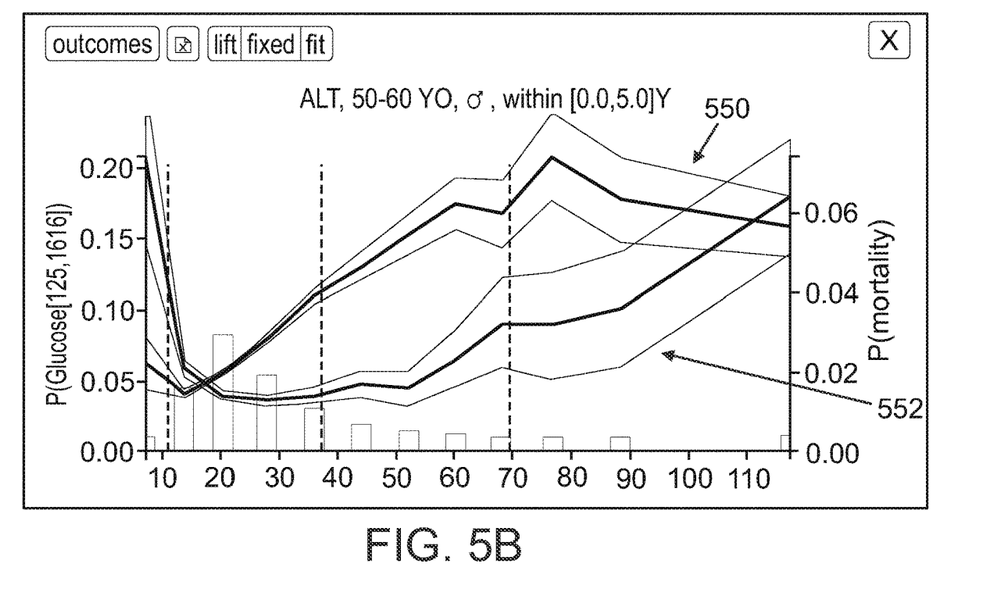

Reference is now made to FIGS. 5A-5B, which are screen captures of another exemplary GUI to navigate associations based on data stored in digital profiles of a dataset, in accordance with some embodiments of the present invention. The screen captures of FIGS. 5A-5B may be created according to the method described with reference to FIG. 3, optionally implemented using system 200 described with reference to FIG. 2, optionally according to instructions described with reference to FIG. 1.

FIG. 5A is a screen capture of an exemplary GUI in which ALT is selected as the test analyte 502. The population is defined according to a selection of male only based on gender 504, and 50-60 for age range 506. The outcome is defined by a 5 year outcome 508 (with selection to filter out those having a follow up of less than 5 years). No drugs have been selected for filter drugs 510. Blood test level and Glucose are selected respectively as outcome type 512 and outcome test 514. The glucose range of 125-1616 is selected as an outcome test range 516. Two (time in a row) outcome test repeats 518 are selected. A first occurrence is selected for an outcome test selection 520.

Field 502 denotes the analyte (i.e., test). Fields 504-506 denotes the defined population. Fields 508-420 denote the clinical outcome.

FIG. 5B is a screen capture of a graph based on the selections using the GUI of FIG. 5A. Graph 550 depicts an association between values of ALT (i.e., analyte) and 5 year risk of developing diabetes defined by 2 consecutive fasting glucose levels equal to or greater than 125 milligram per deciliter (mg/dL) (i.e., outcome) in males age 50-60 (i.e., defined population). Graph 552 depicts an association between values of ALT (i.e., analyte) and 5 year risk of mortality in males age 50-60 (i.e., defined population).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant analyte measurements will be developed and the scope of the term analyte is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method for creating a personalized reference interval (PRI), comprising:
monitoring clinical test results stored by a network connected server;
in response to detecting a clinical test result of a patient added to the network connected server, wherein the clinical test result including a measured value of at least one analyte, wherein a digital profile of the patient includes a combination of a plurality of demographic parameters and associated values, and medical history data parameters and associated values including comorbidity, chronic medical conditions, and current medications:
accessing a dataset storing a plurality of digital profiles of other patients, each digital profile of the dataset is associated with at least one clinical test result of the respective other patient having a statistical distribution including values dissimilar to the measured value of the at least one analyte of the patient, and a combination of the plurality of demographic parameters and associated values for each of the other patients, and medical history data parameters and associated values including comorbidity, chronic medical conditions, and current medications;
identifying a subset of the dataset based a correlation according to a similarity requirement between the combination of at least one of the plurality of demographic parameters and the medical history parameters including comorbidity, chronic medical conditions, and current medications of the digital profile of the patient and at least one of the combinations of the plurality of demographic parameters and the medical history of the other patients including comorbidity, chronic medical conditions, and current medications, wherein the correlation is computed by assigning higher weights to the comorbidity, chronic medical conditions, and current medications, and without consideration to similarity between the measure value of the at least one analyte of the patient and values of the at least one analyte for the digital profiles of other patients;
calculating a personalized reference interval (PRI) for each respective at least one analyte of the clinical test result of the patient according to an analysis of corresponding values of the at least one analyte of the subset, wherein the PRI is dynamically calculated using the dataset;
accessing a standard reference interval (RI) for each respective at least one analyte of the clinical test result of the patient, wherein the standard RI is computed from digital profiles of healthy individuals without comorbidities, without chronic medical conditions, and that are not currently taking medications;
comparing the measured value of the at least one analyte of the clinical test result of the patient with the PRI calculated for the at least one analyte and with the standard RI to determine whether the analyte value of the clinical test result of the patient is representing an underlying clinically significant event or does not represent a clinically significant event;
automatically generating a message including the measured value of the at least one analyte, the PRI, and the standard RI, and an indication of: clinical insignificance when the measured value of the at least one analyte is external to the standard RI and within the PRI, and clinical significance with the measured value of the at least one analyte is within the standard RI and external to the PRI; and
transmitting the message to a client terminal over the network for treatment of the patient according to whether clinical test result represents the underlying clinically significant event or does not represent the clinically significant event.

2. The method of claim 1, wherein the medical history data parameters are indicative of at least one medical pathology.

3. The method of claim 1, wherein the PRI is calculated to account for contradictory effects of demographics and/or medical history on the respective analyte.

4. The method of claim 1, wherein the PRI is calculated to account for additive effects of demographics and/or medical history on the respective analyte.

5. The method of claim 1, wherein the medical history data includes at least one member selected from the group consisting of: past medical history, previous surgeries, smoking status, alcohol consumption status, drug use status, acute medical conditions, family history, and genetic predisposition.

6. The method of claim 1, wherein the analyte is measured from a body fluid selected from the group consisting of: blood, urine, cerebrospinal fluid, pleural fluid, amniotic fluid, aqueous humor, vitreous humor, bile, gastric acid, lymph, mucus, pericardial fluid, pus, saliva, semen, vaginal secretions, sputum, synovial fluid, tears, and sweat.

7. The method of claim 1, wherein the analyte is at least one of: an anatomical body measurement performed directly or using imaging methods, and a measurement of function of an organ.

8. The method of claim 7, wherein the analyte is selected from the group consisting of: body mass index (BMI), cardiac output, respiratory rate, endometrial thickness, appendix size, kidney size, and prostate volume.

9. The method of claim 1, wherein the digital profiles of the subset include at least one of survival of the respective patient and time to a certain clinical outcome occurring to the respective patient, and further comprising calculating a risk for a certain outcome for the patient according to an analysis of the value of the at least one analyte in view of the PRI.

10. The method of claim 9, wherein the certain outcome is at least one of: received from a user using a graphical user interface (GUI), and determined for each of a list of a plurality of predefined outcomes.

11. The method of claim 1, further comprising: receiving at least one another clinical test result of the patient including another measured value of the at least one analyte; determining a trend according to an analysis of difference between the measured value of the at least one analyte of the at least one another clinical test result and the test result; identifying a clinical significance or clinical insignificance of the trend according to the PRI.

12. The method of claim 11, wherein the digital profiles of the subset include at least one of survival of the respective patient and time to a certain clinical outcome occurring to the respective patient, and wherein the identifying the clinical significance or clinical insignificance of the trend is based on calculating a risk for a certain outcome for the patient based on the trend.

13. The method of claim 11, further comprising identifying the clinical significance or clinical insignificance of the trend based on an analysis of a correlation between the trend and a distribution of values corresponding to the trend in the digital profiles of the subset.

14. The method of claim 1, further comprising storing the received clinical result of the patient and digital profile of the patient in the dataset.

15. The method of claim 1, wherein "normal" levels of the at least one analyte of other patients of the dataset defined by the PRI are otherwise abnormal in healthy and normal subjects.

16. The method of claim 1, wherein "abnormal" levels of the at least one analyze of other patients of the dataset defined by the PRI are otherwise normal in healthy and normal subjects.

17. The method of claim 1, wherein the PRI denotes a single unified measure that is calculated to account for contradictory effects of the plurality of demographic parameters and the medical history data parameters of the combination.

18. A system for creating a personalized reference interval (PRI), comprising:
a network connected server in communication with at least one client terminal and with a data storage device storing a dataset storing a plurality of digital profiles of patients, each digital profile of the dataset is associated with at least one clinical test result of the respective patient and a combination of respective values for at least one demographic parameter and medical history data parameters and associated values including comorbidity, chronic medical conditions, and current medications;
a program store storing code; and
at least one processing unit coupled to the server, the data storage device and the program store for implementing the stored code, the code comprising:
code to monitor clinical test results stored by the data storage device;
code to, in response to detecting a clinical test result of a patient added to the network connected server, wherein the clinical test result includes a measured value of at least one analyte, wherein a digital profile of a-the patient includes a combination of at least one demographic parameter and associated value and medical history data parameters and associated values including comorbidity, chronic medical conditions, and current medications, and to receive a clinical test result of the patient, the clinical test result including a measured value of at least one analyte:
code to identify a subset of the dataset based a correlation according to a similarity requirement between the combination of at least one of the plurality of demographic parameters and the medical history parameters including comorbidity, chronic medical conditions, and current medications of the digital profile of the patient and the at least one of the combinations of the plurality of demographic parameters and the medical history of the other patients including comorbidity, chronic medical conditions, and current medications, and calculate a personalized reference interval (PRI) for each respective at least one analyte of the clinical test result of the patient according to an analysis of corresponding values of the at least one analyte of the subset, wherein the PRI is dynamically calculated using the dataset, wherein the clinical test results of the dataset have a statistical distribution including values dissimilar to the measured value of the at least one analyte of the patient, wherein the correlation is computed by assigning higher weights to the comorbidity, chronic medical conditions, and current medications, and without consideration to similarity between the measure value of the at least one analyte of the patient and values of the at least one analyte for the digital profiles of other patients;
code to access a standard reference interval (RI) for each respective at least one analyte of the clinical test result of the patient, wherein the standard RI is computed from digital profiles of healthy individuals without comorbidities, without chronic medical conditions, and that are not currently taking medications;
code to compare the measured value of the at least one analyte of the clinical test result of the patient with the PRI calculated for the at least one analyte and with the standard RI to determine whether the analyte value of the clinical test result of the patient is representing an underlying clinically significant event or does not represent a clinically significant event;
code to automatically generate a message including the measured value of the at least one analyte, the PRI, and the standard RI, and an indication of: clinical insignificance when the measured value of the at least one analyte is external to the standard RI and within the PRI, and clinical significance with the measured value of the at least one analyte is within the standard RI and external to the PRI; and
code to transmit the message to the at least one client terminal over the network for treatment of the patient according to whether clinical test result represents the underlying clinically significant event or does not represent the clinically significant event.

* * * * *